United States Patent [19]

Tidd et al.

[11] 4,199,261
[45] Apr. 22, 1980

[54] OPTICAL INTENSITY METER

[75] Inventors: Leon E. Tidd, San Francisco; Alan B. Scott, Mill Valley; Julius M. J. Madey, Fairfax; Carter C. Collins, Mill Valley, all of Calif.

[73] Assignee: Smith-Kettlewell Eye Research Foundation, San Francisco, Calif.

[21] Appl. No.: 755,332

[22] Filed: Dec. 29, 1976

[51] Int. Cl.$^2$ ............................................. G01N 21/48
[52] U.S. Cl. ..................................................... 356/448
[58] Field of Search ............... 356/173, 201, 209, 211, 356/212, 206, 402, 432, 435, 445, 447, 448; 250/559, 571

[56] References Cited

U.S. PATENT DOCUMENTS

| | | | |
|---|---|---|---|
| 3,430,055 | 2/1969 | Metzger | 356/237 |
| 3,659,943 | 5/1972 | Goolsby | 356/212 |
| 3,796,500 | 3/1974 | Obser | 356/237 |
| 3,918,815 | 11/1975 | Gadbois | 356/206 |
| 3,919,531 | 11/1975 | Bobel et al. | 356/237 |
| 3,920,402 | 11/1975 | Afanasier et al. | 356/209 |
| 3,937,614 | 2/1976 | Sodickson et al. | 356/209 |
| 4,003,662 | 1/1977 | Retzer et al. | 356/206 |

FOREIGN PATENT DOCUMENTS 2454644  11/1976  Fed. Rep. of Germany ........... 356/209

Primary Examiner—John K. Corbin
Assistant Examiner—R. A. Rosenberger
Attorney, Agent, or Firm—David E. Lovejoy

[57] ABSTRACT

A meter and method for measuring the intensity of reflected or other light. The meter is particularly suitable for use by blind or visually impared diabetics to determine sugar level in their urine and in one embodiment is a handheld, battery-powered, audio-output device. A chemical impregnated sample under test is illuminated with a light source and reflected light is detected to form an electrical measurement signal. In order to minimize variations in light source output, the measurement signal is typically formed as a ratio of logrithmically scaled signals derived from the sample under test and from the light source. The measurement signal is compared with reference levels and the comparison results are encoded to provide signals to an audio or other indicator. A time sequencer is provided for causing the measurement signal to be examined at a predetermined time.

23 Claims, 3 Drawing Figures

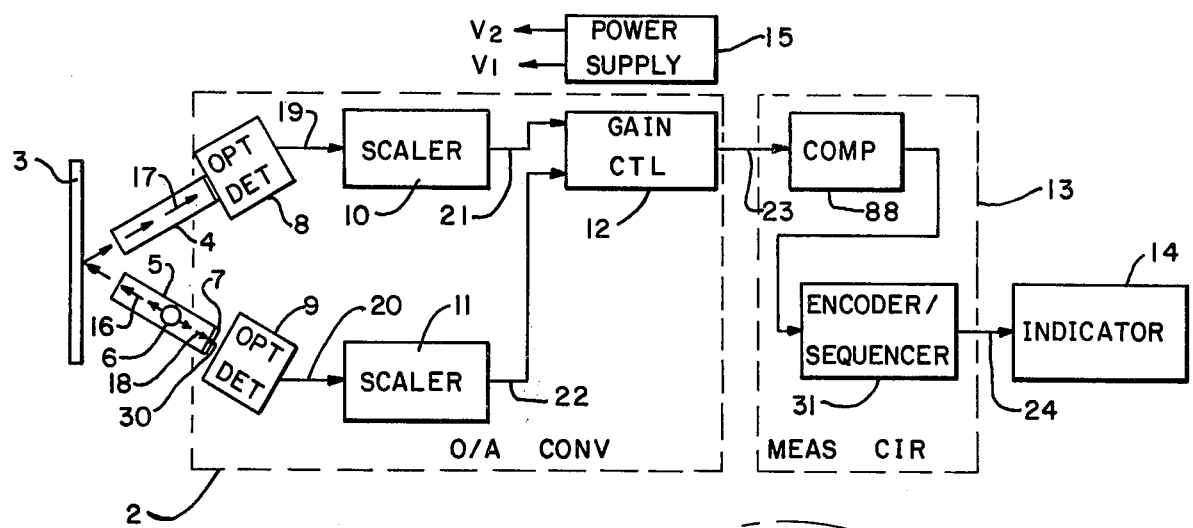
FIG.—1
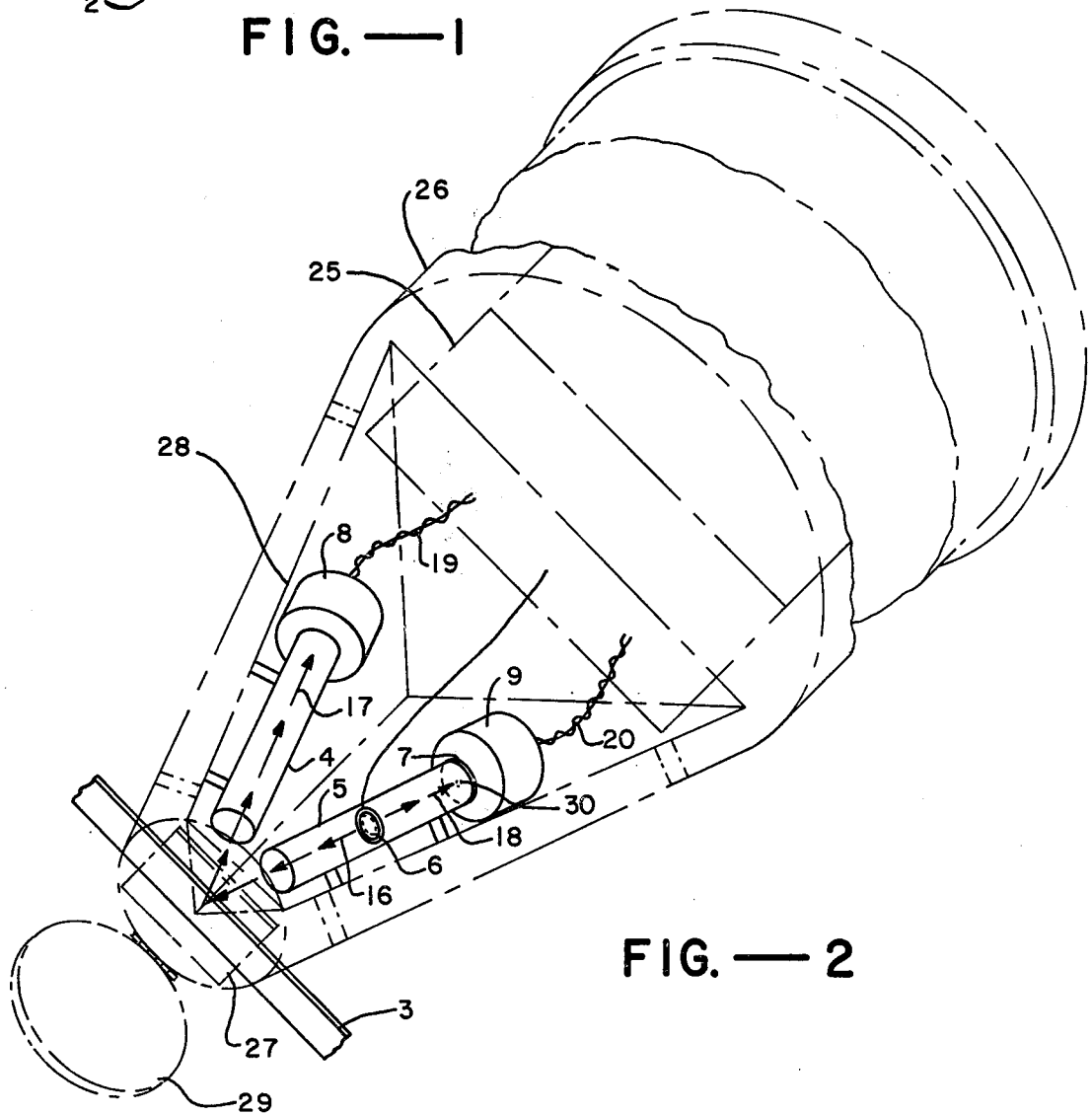
FIG.—2

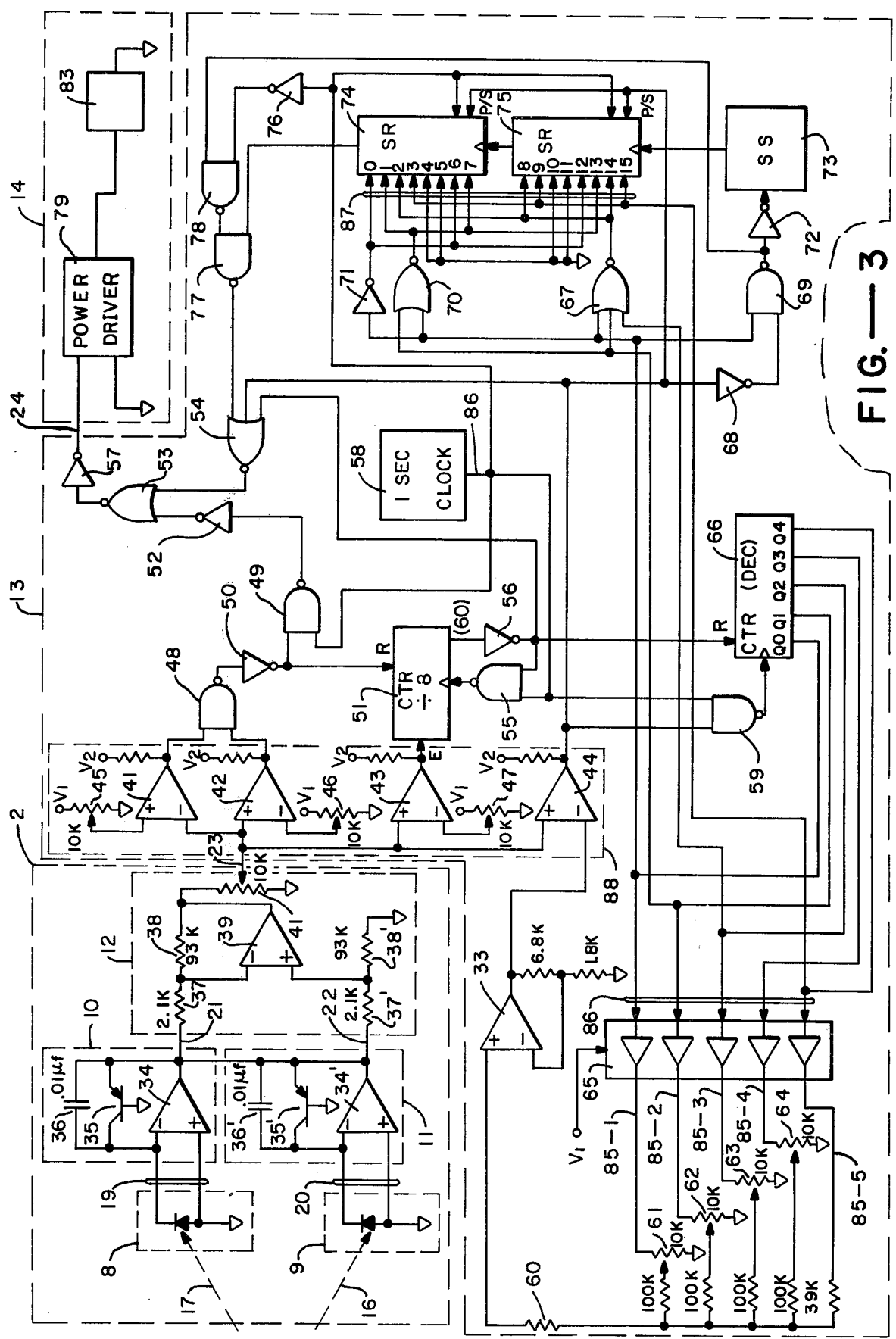
FIG.—3

OPTICAL INTENSITY METER

BACKGROUND OF THE INVENTION

Diabetes is a significant problem among blind people and diabetes is a significant cause of blindness. The incidence of blindness increases in older people so that as the life expectancy of diabetic people increases, blindness becomes an increasing problem. In light of these well-known medical facts, there is a need for apparatus to enable blind, visually impared and other people to perform urine glucose tests reliably and without assistance from others.

Chemically impregnated test devices are available for making urine glucose tests. For example, the "Test-Tape" paper of the Eli Lilly Company and the "Uristix" stick of the Ames Company are commercially available test devices. These test devices, when placed in urine, undergo a chemical reaction. The chemical reaction is one in which there is a reduction of an impregnated cooper substance from the cupric to the cuprous state as a function the sugar level in the urine. The reduction causes an attendant development of an orange pigment. The reaction, and hence the sugar level in the urine, is measured as a function of the reflectance (or transmittance) of the test device at a specified time following contact with the urine.

While these test devices can be used by people having normal vision, blind and visually impared people cannot see the pigment change and therefore cannot utilize these test devices without assistance. There is a need, therefore, for an intensity meter which is capable of measuring the intensity of chemically impregnated test materials.

In addition to the specialized need to provide intensity meters capable of use by blind people, a broader need also exists for improved intensity meters which are compact and economical and which are accurate notwithstanding changes of intensity in the light source.

SUMMARY OF THE INVENTION

The present invention is an optical intensity meter and a method of dectection. The meter includes a light source for illuminating a test sample. In accordance with the method, light from the sample is detected to form an electrical measurement signal. The measurement signal is compared with reference levels in a comparator. Outputs from the comparators are encoded to provided drive signals for an indicator for indicating optical properties of the test sample.

In accordance with one embodiment of the present invention, a sample detector detects light from the test sample to form a sample signal and a source detector detects light directly from the light source to form a source signal. A measurement signal is formed as the ratio of the sample and source signals.

In one embodiment of the present invention, the sample and source signals are scaled to provide for a large operating range for reflected light. The scalers are preferably logarithmic scalers.

In one embodiment, collimators are provided for collimating the light from the light source to the test sample, for collimating light from the sample to the sample detector, and for collimating light from the light source to the source detector.

In one embodiment, a measurement circuit is provided for analyzing the measurement signal. The measurement circuit includes an analog-to-digital converter. The converter is formed, for example, by one or more comparators for comparing the measurement signal with reference levels for detecting a plurality of different amplitudes for the measurement signal. The comparator outputs are digital signals which are encoded in encoder circuitry to provide drive signals for the indicator. In one embodiment, the measurement circuit also includes a time sequencer for analyzing the measurement signal at predetermined times and for controlling the encoder circuitry.

In one embodiment, the measurement signal is detected for determining a pretest condition such as dry paper in the case of a urine-sugar test. In accordance with another feature, a timing period is initiated when the beginning of a test is detected. Such a beginning occurs, for example, when a wet paper condition is detected in a urine-sugar test. After detecting the beginning of a test, the sequencer causes the measurement signal to be analyzed using the comparators to determine if the measurement signal is within predetermined limits.

An indicator is provided for indicating the level of the measurement signal. In accordance with one embodiment, the indicator provides an audible signal.

In accordance with one embodiment, the optical apparatus and the measurement circuit are constructed to form a portable, hand-held, battery-powered device. These features together with the audible output render the intensity meter suitable for use by blind diabetics and the visually impaired. As a further feature in one embodiment, the measurement circuit and optical apparatus are turned on by the operation of inserting a dry test sample. The indicator provides a signal to indicate that a dry pre-test sample condition has been established properly for the test sample.

In accordance with the above summary, the present invention achieves the objective of providing in general an improved intensity meter and specifically one which is suitable for use by blind diabetics in performing urine glucose tests.

Additional objects and features of the invention will appear from the following description in which the preferred embodiments of the invention have been set forth in detail in conjunction with the drawings.

BRIEF DESCRIPTION OF THE DRAWINGS

FIG. 1 depicts a block diagram representation of the intensity meter in accordance with the present invention.

FIG. 2 depicts a detailed mechanical drawing of the optical apparatus which forms a portion of the intensity meter of FIG. 1.

FIG. 3 depicts a schematic representation of the electrical apparatus which forms a portion of the FIG. 1 intensity meter.

DETAILED DESCRIPTION

In FIG. 1, the test sample 3 is positioned in close proximity to the optical-to-analog converter (O/A CONV) 2 to receive illumination from the light source 6. Light travels from the source 6 to the test sample 3 along an optical path 16. Collimator 5 collimates light traveling along the optical path 16. Light is reflected from sample 3 and travels along path 17, through collimator 4, to an optical detector 8. Light from source 6 also travels through collimator 5, along light path 18, and through attenuator 7 to an optical detector 9. Optical detector 8 detects light on path 17 from the sample 3 and responsively forms an electrical sample signal on line 19. Optical detector 9 detects light on path 18 from the source 6 and responsively forms an electrical source signal on line 20. Optical detectors 8 and 9 typically are light-sensitive diodes or other conventional detectors which provide signals on output lines 19 and 20, respectively, with amplitudes which vary as a function of the intensity of the light incident upon the detectors.

The electrical signal on line 19 is input to a scaler 10 which scales the amplitude of the sample signal on line 19 to form a scaled sampled signal on line 21. In a similar manner, scaler 11 scales the source signal on line 20 to form a scaled source signal on line 22. In one preferred embodiment, the scalers 10 and 11 are logarithmic scalers.

The scaled signals on lines 21 and 22 are input to a difference amplifier circuit 12 which functions to produce an output measurement signal on line 23 which is a ratio of the signals on lines 19 and 20. The measurement signal on line 23 has an amplitude which is independent of changes in light intensity of the light source 6. In this manner, the measurement signal on line 23 provides an accurate measurement of the intensity of light received from the sample 3.

Where less accuracy is tolerable, the optical-to-analog converter 2 may employ alternative apparatus. For example, the scalers 11 and 12 may be eliminated thereby reducing the range overwhich operation is possible. Also, the source detector 9 and the input on line 22 may be eliminated where changes in the light source are not critical.

The measurement circuit 13 receives the measured signal on line 23, measures the level of that signal and provides an indication thereof on line 24. The signal on line 24 is in turn utilized to energize the indicator 14.

The measurement circuit 13 includes a comparator 88 for comparing the measurement signal on line 23 with a number of reference levels. The outputs from comparator 88 provide an input to encoder/sequence 31. Encoder/sequencer 31 encodes the outputs from comparator 88 to provide, at a proper sequence time, drive signals to the indicator 14. The encoder/sequencer 31, in one embodiment hereinafter described, includes a time-serial encoder with a sequencer which establishes predetermined measurement times and controls the encoding. Alternatively, conventional parallel encoding of the comparator 88 output may be employed.

In FIG. 1, the power supply 15 in a portable embodiment is a model A D 580 manufactured by Analog Devices, Inc.

In FIG. 2, a portable embodiment of an optical intensity meter in accordance with the present invention is shown. In FIG. 2, the optical apparatus is located within the cone-shaped portion of body 26. The optical apparatus includes the optical detectors 8 and 9 which are located to receive light from the collimators 4 and 5, respectively. In one embodiment, collimators 4 and 5 are each metal rods approximately ⅜ of an inch in length and ¼ inch in diameter. The collimator 5 has an incandescent light 6 positioned through a hole in the wall of collimator 5. The hole is located approximately midway between the ends of collimator 5. The dectors 8 and 9 are collimators 4 and 5 are rigidly secured to a tripod frame 28 which is internal to the body 26. The collimators 4 and 5 and the detectors 8 and 9 are located such that the optical axis 16 intersects the plane of sample 3 with an angle which equals the angle at which the optical axis 17 intersects the sample 3. The optical axis 16 and 17 meet within a small test region on sample 3. Sample 3 is positioned adjacent a window 27. Window 27 is formed of a transparent or translucent material such as plastic. A hinged cover 29 is provided which swings over the end of the cone-shaped end of body 26 to provide a backing for sample 3 and to hold it in position in front of the window 27.

The optical axis 18 is a path for light from the lamp 6 to the detector 9. Within this optical path, a pinhole filter 7 is located between the end of the tube 5 and the detector 9. The filter 7 has a pinhole 30 which reduces the quantum of light from lamp 6 which impinges upon the detector 9. The reduction by filter 7 functions to attenuate the light and causes the quantum of light incident to detector 9 to be of the same order of magnitude as the light incident on detector 8.

For non-portable embodiments, the mechanical and optical housing of FIG. 2 may take many other conventional configurations. For example, a rectangular table-top enclosure may be suitably employed.

In FIG. 2, the electronics portion of the intensity meter of FIG. 1 is conveniently located within the cylindrical portion of the body 26. Body 26 extends to a length (shown broken) sufficient to house the electronics, including the battery and other power supply apparatus.

In FIG. 3, a schematic electrical diagram is shown of one detailed embodiment of the electrical portion of the FIG. 1 apparatus. The optical detectors 8 and 9, the scalers 10 and 11, the difference amplifier 12, the measurement circuit 13 and the indicator 14 correspond to the like-numbered elements in FIG. 1.

In FIG. 3, the optical detecotrs 8 and 9 are each conventional light-sensitive diodes which provide output signals on lines 19 and 20, respectively, proportional in amplitude to the light received on paths 17 and 16, respectively. While light-sensitive diodes are preferred in a portable, battery-powered device, other conventional optical detectors can be employed within the scope of the present invention.

The signal on lines 19 is input to a differential amplifier 34. Amplifiers 33, 34 and 39 in one embodiment, are model LM 324 manufactured by National Semiconductor Corp.

The scaler 10 includes an amplifier 34 with a transistor 35 and a 0.01 microfarad capacitor 36 connected in parallel between its input and output. The amplifier 34, transistor 35 and capacitor 36 scale logarithmically the sample signal on lines 19 to form the signal on line 21. A logrithmic scalling is preferred in that variations in light intensity from the test sample 3 tend to change logarithmitically and therefore the characteristics of scaler 10 tend to match intensity changes expected from the test sample 3. Of course, scaler with different scalling functions can be employed within the spirit of the present invention.

The scaler 11 includes components like those in scaler 10 with the corresponding components identified with corresponding primed numbers.

In FIG. 3, the gain control circuit 12 includes input 1K resistors 37 and 37' in the input lines 21 and 22, respectively. The input resistors 37 and 37' in turn connect to the differential inputs of an amplifier 39. In one embodiment, amplifier 39 is of the same type as amplifier 34. A 93K resistor 38 is connected in the feedback loop from the output to the negative input of amplifier 39. In a symmetrical manner the 93K resistor 38' is connected to ground. The output from amplifier 39 is a signal formed by the ratio of the sample signal on line 19 and the source signal on line 20. In this manner, variations in the signal from amplifier 39 which result from variations in intensity of the source 6 in FIG. 1 are removed or minimized.

The signal from amplifier 39 is connected through a 10K resistor 41. Resistor 41 through its variable-tap provides for gain adjustment of the measurement signal on line 23. The output from amplifier 39 for a dry test sample is approximately 500 millivolts and is reduced to approximately 100 millivolts on line 23 by resistor 41.

The measurement signal on line 23 is input to the comparator circuit 88 within the measurement circuit 13. The comparator circuit 88 includes four comparators 41, 42, 43 and 44. The comparators 41 through 44 in one embodiment are models LM 339 manufactured by National Semiconductor Corp.

The comparators 41 through 44 are provided for detecting predetermined levels in the measurement signal on line 23. The levels detected by the comparators 41, 42 and 43 are established by the reference levels determined by the variable-tap 10K resistors 45, 46 and 47, respectively. The variable-tap resistors 45 through 47 are connected between a +V1 power supply voltage and ground.

In FIG. 3, the tap for resistor 45 is set to establish an approximately 175 millivolt threshold reference level for comparator 41. Whenever the signal on line 23 is less than 175 millivolts, comparator 41 has a logical 1 output and otherwise has a logical 0 output.

The tap for resistor 46 is set to establish an approximately 20 millivolt threshold reference level for comparator 42. When the signal on line 23 is greater than 20 millivolts, the output from comparator 42 is a logical 1 and otherwise is a logical 0. Together, the comparators 41 and 42 provide logical 1 outputs whenever the signal on line 23 is greater than 20 millivolts and less than 175 millivolts.

The comparators 41 and 42 function as a dry paper detector to determine when the test sample 3 is inserted into the optical path 16 in the dry condition. Whenever these conditions are satisfied, the NAND gate 48 provides a 0 output which is inverted in inverter 50 to a 1. A 1 from inverter 50 resets the counter 51 and provides an enable input to NAND gate 49.

The resistor 47 has its tap set to provide a threshold reference level of approximately 800 millivolts. Whenever the measurement signal on line 23 is greater than approximately 800 millivolts, comparator 43 provides a logical 1 output which enables the 8-bit binary counter 51. Comparator 43 functions as a wet paper detector to determine when the test sample 3 of FIG. 1 is in the wet condition, which is a beginning-of-test condition.

In FIG. 3, the comparator 44 compares the amplitude of the measurement signal on line 23 with theshold levels established by the amplifier 33. Amplifier 33 sequentially provides, at its output, five different threshold levels, that is, five test reference levels. Comparator 44 sequentially detects whether the measurement signal on line 23 exceeds each of those five threshold levels. In one embodiment, the amplifier 33 is the same type as amplifier 34 in the scaler 10.

The five threshold levels sequentially established at the positive input of amplifier 33 result from five sequential outputs from buffer bank 65. Buffer bank 65, in one embodiment, is an RCA model CD 4009. The first four outputs 85-1, 85-2, 85-3 and 85-4 from buffer bank 65 connect through the level setting variable taps from the 10K resistors 61, 62, 63 and 64, respectively, from the 100K resistors to the 1.5K resistor 60. The fifth output 85-5 from buffer bank 65 connects directly from the buffer bank through a 39K resistor to the 1.5K resistor 60. Resistor 60 connects as the positive input to non-inverting amplifier 33. Only one of the five buffers of bank 65 is active at any given time as controlled by a selected one of the input lines 86. When the first buffer is active, line 85-1 connects resistor 61 as the input to amplifier 33. The tap on resistor 61 is set so as to cause an output from amplifier 33 to establish a "wet paper" threshold level of approximately 800 millivolts.

Resistor 62 has its tap set so that, when selected by the second buffer via line 85-2, the output from amplifier 33 is a threshold of approximately 1.5 volts.

The tap for resistor 63 is set so that, when selected by the third buffer via line 85-3, the output from amplifier 33 is a threshold level of approximately 1.8 volts.

The tap for resistor 64 is set so that, when selected by the fourth buffer via line 85-4, the output from amplifier 33 is a threshold level of approximately 2.2 volts.

The output through the 47K resistor, when selected by the fifth buffer via line 85-5, causes amplifier 33 to provide a threshold level of approximately 5 volts. The 5 volt threshold always exceeds the amplitude of the measurement signal on line 23.

The determination of which one of the five buffers in buffer bank 65 is selected is determined by the five outputs Q0, Q1, Q2, Q3 and Q4 from the decade counter 66. Counter 66 is stepped by the output from a one second clock line 86 when NAND gate 59 is enabled. When counter 66 is clocked, a logical 1 is serially stepped through each of the outputs Q0 to Q4 to serially enable each of the lines 85-1 to 85-5, respectively, through the buffers in buffer bank 65.

The decade counter 66 is any conventional counter for providing outputs Q0 through Q4 one at a time. In the embodiment of FIG. 3, counter 66 includes two or more stages (not shown) of lower-order than the Q0 stage. Those lower-order stages are stepped, prior to the stepping of Q0, by operation of the clock input from NAND gate 59. The lower-order stages provide a momentary delay before the Q0 output is energized. Whenever the signal from inverter 56 is a 1, decade counter 66 is held in a reset condition with all of the outputs Q0 through Q4 held as 0's. When NAND gate 59 is enabled with a 1 from comparator 44, clock pulses from clock line 86 are input to the counter 66. When the reset signal from inverter 56 is switched to 0, counter 66 commences counting the clock pulses passed through gate 59. After the lower-order stages (not shown) are switched to 1's, 1's are propagated through stages Q0 to Q4 one at a time and in order unless the output from comparator 44 goes to 0 and thus disables NAND gate 59.

Clock 58 is a conventional device which provides one output clock pulse each second on output line 86. The clock pulses have a one second clock period where each period has a 1 portion and a 0 portion.

Counter 51 is a conventional 8-bit binary counter which includes a clock input from NAND gate 55, an enable input from comparator 43, a reset input from inverter 50 and a count 60 output connected to inverter 56. Counter 51 counts clock pulses from gate 55 whenever the output from comparator 43 is a 1 and the reset level from inverter 50 is a 1. When enabled by the output from comparator 43, counter 51 counts a total of sixty one-second pulses from clock 58 and is therefore a one-minute counter. An output 1 signal to inverter 56 occurs one minute after the counter is enabled and that 1 is inverted in inverter 56 to a 0. That 0 removes the reset from decade counter 56 while inhibiting further clock pulses from being propagated through NAND gate 55 to counter 51. Also a 0 from inverter 56 provides an enable input to NOR gate 54.

In FIG. 3, two 8-bit shift register stages 74 and 75 form a 16-stage shift register 74–75 with stages designated SR0, SR1, ..., SR15. In FIG. 3, SR0 is the topmost stage of shift register 74 and SR15 is the bottommost stage of shift register 75. The shift register stages are parallel loaded by the sixteen lines 87 whenever the parallel/serial control line from comparator 44 is a 0. Whenever the control line from comparator 44 is a 1, the shift register is in the serial mode and the contents of the sixteen stages are serially shifted out from SR15 through SR0 to NAND gate 77. Simultaneously while shifting data serially out to gate 77, data is serially shifted in from SR15 to SR0 with 1's or 0's as controlled by the non-retriggerable single-shot 73. The shifting of data is caused to occur by clock signals on the clock line 86.

The data which is parallel loaded into the shift register 74–75 is determined by the Q0 through Q4 outputs of decade counter 66, NOR gates 67 and 70, and inverter gate 71. As long as the output from comparator 44 remains a 1, data is parallel loaded into the shift register 74–75 during each clock pulse on line 86. Counter 66 and gates 67, 70 and 71 are a serial encoder for encoding the output from comparator 44 into the shift register 74–75. Counter 51, buffer bank 65 and comparator 33, together with the interconnecting circuitry, form a sequencer for sequencing the serial encoder.

Five states are loaded into shift register 74–75, one for each of the five outputs Q0, Q1, ..., Q4 from the decade counter 66. The five states are shown in the following TABLE I.

TABLE I

| | SR 15 | SR 14 | SR 13 | SR 12 | SR 11 | SR 10 | SR 9 | SR 8 | SR 7 | SR 6 | SR 5 | SR 4 | SR 3 | SR 2 | SR 1 | SR 0 |
|---|---|---|---|---|---|---|---|---|---|---|---|---|---|---|---|---|
| Q0 | 0 | 0 | 0 | 0 | 0 | 0 | 0 | 0 | 0 | 0 | 0 | 0 | 0 | 0 | 0 | 0 |
| Q1 | 0 | 0 | 0 | 1 | 0 | 0 | 0 | 0 | 0 | 1 | 0 | 0 | 0 | 0 | 0 | 1 |
| Q2 | 0 | 0 | 1 | 1 | 0 | 0 | 0 | 0 | 1 | 1 | 0 | 0 | 0 | 0 | 1 | 1 |
| Q3 | 0 | 1 | 1 | 1 | 0 | 0 | 0 | 1 | 1 | 1 | 0 | 0 | 0 | 1 | 1 | 1 |
| Q4 | 1 | 1 | 1 | 1 | 0 | 0 | 1 | 1 | 1 | 1 | 0 | 0 | 1 | 1 | 1 | 1 |

In TABLE I the Q0 entry on the left-hand margin designates that the Q0 output from counter 66 is a 1 while all other outputs are 0. Under these conditions, the Q0 output to NOR gates 67 and 70 forces each of their outputs to 0. Also, the 1 for Q0 is directly inverted to inverter 71 to provide a 0 output. Since all of the outputs from gates 67, 70 and 71 are 0, all of the locations in the shift register 74–75 are loaded with 0's. The shift register locations SR4, SR5, SR10 and SR11 are always loaded with 0's in all five states of TABLE I.

In TABLE I, the Q1 entry on the left hand margin signifies that Q1 is 1 while all other outputs from counter 66 are 0. Under this condition, the Q1 input to gates 67 and 70 forces their outputs to 0. However, the 0 for Q0 is inverted in inverter 71 to 1. Under these conditions, the locations SR0, SR6, and SR12 which receive the outputs of inverter 71, are loaded with 1's while all other locations store 0's.

In TABLE I, the Q2 condition causes the output from gate 67 to be 0 while the outputs from gates 70 and 71 are 1. Under these conditions, locations SR0 and SR1, locations SR6 and SR7, and locations SR12 and SR13 store 1's while all other locations store 0's.

In TABLE I, when Q3 is 1, all of the gates 67, 70 and 71 provide a 1 output while the Q4 output is still zero. Accordingly, the locations SR0, SR1, and SR2, the locations SR6, SR7 and SR8, and the locations SR12, SR13 and SR14 store 1's while the remainder of the locations store 0's.

In TABLE I when Q4 is 1, the gates 67, 70 and 71 have 1 outputs. Under these conditions only the locations SR4 and SR5 and the locations SR10 and SR11 are loaded with 0's while all other locations are loaded with 1's.

Whenever the comparator 44 output goes from 1 to 0, the output state of counter 66 remains at one of the values Q0 through Q4. If the counter is not stopped before it reaches Q4, the Q4 threshold value input to comparator 44 is designed to insure that the comparator output will go to 0. When the comparator output goes to 0, it places shift register 74–75 in the serial mode.

In the serial mode, the sixteen locations SR0 through SR15 are stepped out in order to gate 77. The shift register is stepped when each clock pulse on line 86 goes positive. When each clock pulse goes negative, NAND gate 78 is enabled for the remainder of the clock pulse period. NAND gate 77 is satisfied to produce an 0 output for each 1 output from the shift register 74–75. For example, if counter 66 stops at the Q1 count, the output from gate 77 is three 0 pulses each of which has a duration which is equal to the 0 portion of one clock pulse. The three pulses occur when the SR0, SR6, and SR12 locations are gated out.

If counter 66 stops with a 1 on the Q3 output, then a total of nine 0 pulses are output through gate 77. The nine pulses occur in three groups of three. The first three pulses occur when the SR0, SR1 and SR2 locations are gated out from the shift register during three consecutive clock pulses. The next group of three occur when the SR6, SR7 and SR8 locations are gated out three clock pulses after SR0, SR1 and SR2. The final group of three are gated out three clock pulses later when the SR12, SR13 and SR14 locations are gated out. Each of those nine pulses has a duration equal to the 0 portion of one clock period and each pulse appears as a 0 from NAND gate 77. Those 0 pulses from gate 77 are propagated through the NOR gate 54 provided that gate 54 is enabled by 0 levels from inverter 56 (one minute time) and comparator 44 (threshold).

NOR gate 54 connects its output to NOR gate 53. Gate 53 propagates pulses from gate 54 provided that the output from inverter 52 is 0. Alternatively, gate 54 propagates pulses from inverter 52 provided the output from gate 54 is 0.

Whenever gate 53 propagates pulses, they are inverted in inverter 57 and input to a conventional power driver 79 which provides signals to the annunciator 83. Annunciator 83 is typically model DA 505 manufactured by Projects Unlimited of Dayton, Ohio. Annunciator 83 makes an audible sound for each pulse output through gate 53.

One input to NOR gate 53, through inverter 52, is provided by the NAND gate 49. NAND gate 49 is enabled with a 1 from inverter 50 whenever the measurement signal on line 23 is in the "dry paper" range detected by comparators 41 and 42. When enabled with a 1 from inverter 50, NAND gate 49 is alternately satisfied to provide 0 pulses during the 1 portion of each clock pulse on line 86 and unsatisfied to provide 1 pulses during the 0 portion of each clock pulse.

These 0 pulses alternating with 1 pulses through inverter 52, alternately satisfy NOR gate 53 provided that NOR gate 53 is enabled, by NOR gate 54, with a 0. The result is that whenever the "dry paper" condition is detected, the indicator circuit 14 is enabled to continuously output alternate on and off signals each one-second clock period. The alternate on and off signals indicate a pretest "dry paper" condition.

In FIG. 3, the NAND gate 69 is enabled when the Q0 output of counter 66 is 1. If when the Q0 is 1, the output from comparator 44 goes to 0 and is inverted in inverter 68 to 1, gate 69 is satisfied to produce a 0 output which is in turn inverted in inverter 72 to clock the non-retrigerable single-shot 73. At the same time, the 0 output from gate 69 forces the output of gate 78 to 1 so that NAND gate 77 is continuously enabled. With the output from comparator 44 a 0, the shift register 74–75 is in the serial mode and is storing all 0's. The 0's are serially shifted out from the shift register 74–75 by operation of the clock 86 through the enabled NAND gate 77. The all 0's output does not cause the indicator 14 to give any signal for the duration of sixteen clock periods which are required to empty the shift register 74–75. While the 0's are being stepped out of the shift register, the single-shot is still timing out and providing a 1 on the serial input to stage 75. Accordingly, as the sixteen 0's are stepped out, sixteen 1's are stepped continuously into the shift register. Also, additional 1's are stepped in as long as the output from the single-shot remains a 1. Those 1's continue to be stepped through the shift register and through the NAND gate 77, gate 54, gate 53 and inverter 57 to the indicator 14. When the 1's are received by the indicator 14, they cause the indicator to give a continuous signal until single-shot 73 returns to 0 and all of the 1's loaded into the shift register 74–75 have been transferred out through the indicator. If single-shot 73 has a 20 second time-out, the indicator 14 provides approxmiately a continuous 20 second signal.

SUMMARY OF OPERATION

In order to commence operation of the intensity meter, a dry paper test sample is inserted as the test sample 3 in the position generally indicated in FIG. 1. The sourece 6 illuminates the paper so that a measurement signal is provided on line 23 output from the optical-to-analog converter in the manner previously indicated.

The measurement signal for a dry paper will be detected with an amplitude falling between the limits established by comparators 41 and 42 in the measurement circuit 13 of FIG. 3. When a dry paper signal level is detected, in FIG. 3, NAND gate 48 is satisfied and enables NAND gate 49. Gate 49 then alternately is satisfied by the 1 and 0 switching of the clock pulse line 86 which, in turn, through NOR gate 53, provides an on and off signal to the indicator 14. Indicator 14 responsively provides an on and off audiable tone having the frequency of the one second clock signal on line 86.

Thereafter, when the test sample 3 becomes wet by emersion in urine, a new "wet paper" amplitude level occurs for the measurement signal on line 23. The "wet paper" level is detected by comparator 43. Comparator 43 responsively enables the binary counter 51 while NAND gate 48 is also disabled to terminate the dry paper signal from annunciator 83. Counter 51 then counts clock pulses propagated through NAND gate 55 until the 60 second count is reached to provide an output 0 signal through inverter 56. The 0 output from inverter 56 inhibits gate 55 and prevents any further clock signals from being counted by counter 51. At the same time, the NOR gate 54 is enabled and the reset from decade counter 66 is removed. At this time, the output of comparator 44 is still 1 so that NAND gate 59 transmits clock pulses to counter 66. When the Q0 output of counter 66 goes to 1, line 85-1 from the buffer bank 65 is energized to provide a first threshold to comparator 44 and to load all 0's into shift register 74–75. If at this time, the threshold signal from comparator 33 exceeds the level of the measurement signal on line 23, then the NAND gate 69 functions to trigger the single-shot 73 while the shift register is serially stepped to provide a drive signal for causing a silent pause followed by a long audible signal (20 seconds) from the indicator 14 to indicate a "below scale" reading. Assuming, however, that in the present example, the output from comparator 44, after the first threshold test, still remains 1, another clock pulse through gate 59 steps the counter 66 Q1 output to 1. The Q1 output selects line 85-2 from buffer bank 65 and provides a second threshold level to the comparator 44. At the same time, the Q1 encoded values of TABLE I above are entered into the shift register 74–75.

Assuming that after the Q1 threshold test the comparator 44 output still remains 1, another clock pulse is input to counter 66 and the Q2 threshold test is performed. The threshold tests continue until the output from comparator 44 is 0 indicating that the threshold level from amplifier 33 is greater than the measurement signal on line 23. If that comparison does not occur on any of the threshold tests from Q0 to Q3, then by circuit design it does happen on the Q4 threshold test. On whichever one of the Q0 through Q4 outputs the comparator 44 output goes to 0, the shift register 74–75 is switched to the serial mode and the contents of the shift register 74–75 are serially counted out through the NAND gate 77. If the count is any count from Q1 to Q4, then the number of short pulses indicated by 1's in TABLE I are shifted out to the indicator 14.

A blind person or any other person, by listening to the audible output from the annunciator 83, may count the number of pulses and thereby determine what measurement level has been detected by the intensity meter of the present invention.

While the present invention has been described in connection with a particular measurement circuit connected to an audio indicator which provides an audio output, other embodiments of the invention may employ different components.

For example, the measurement circuit may be a conventional moving arm meter or an analog-to-digital converter. Where an analog-to-digital converter is employed, the analog signal on line 23 is converted to a digital value. That digital value may be utilized directly or may be encoded to provide a digital readout. The digital readout may be enabled only after a one minute or other time period in the manner controlled by the counter 51 in the embodiment described. In the present embodiment of FIG. 3, the comparator circuit 88 is one form of an analog-to-digital converter. The analog level on line 23 is converted to a logical 1 or 0 digital level at the output of comparator 44.

While the invention has been particularly shown and described with reference to preferred embodiments thereof, it will be understood by those skilled in the art that various changes in form and details may be made therein without departing from the spirit and the scope of the invention.

What is claimed is:

1. Apparatus for use by visually impared people for detecting an optical measurement level of a test sample comprising:
    light source means for illuminating the test sample to cause light to emanate from the test sample to form the optical measurement level as a function of an optical property of the test sample and of the illuminating light,
    an optical-to-analog converter for converting the light emanating from the test sample to an electrical analog measurement signal having an amplitude proportional to said optical measurement level,
    measurement circuit means for measuring said measurement signal in relation to a plurality of different reference levels to provide a plurality of digital signals representing whether or not the measurement signal exceeds the reference levels, respectively,
    said measurement circuit means including a plurality of comparators for comparing said measurement signal with said plurality of different reference levels thereby detecting the amplitude of said measurement signal between one or more pairs of said reference levels;
    said plurality of comparators including first and second comparators simultaneously receiving said measurement signal for comparing said measurement signal with first and second reference levels, respectively, and including means for generating said first and second reference levels to establish a pretest optical measurement level for said test sample;
    said plurality of comparators including a third comparator receiving said measurement signal for comparing said measurement signal with a third reference level and including means for generating said third reference level to establish a beginning-of-test optical measurement level for said test sample;
    indicator means responsive to said digital signals for providing an indication, detectable by visually impared people, of said optical measurement level.

2. The apparatus of claim 1 wherein said plurality of comparators within said measurement circuit means includes comparator means for comparing said measurement signal with one or more test reference levels, test reference level generation means for generating said one or more test reference levels.

3. The apparatus of claim 2 wherein said generation means includes means for selectively generating a plurality of test reference levels and wherein said measurement circuit means includes sequencer means for sequencially selecting said test reference levels in said generation means one at a time whereby said comparator means sequentially compares the amplitude of said measurement signal with said plurality of test reference levels to detect the optical measurement level of the test sample.

4. The apparatus of claim 3 wherein said sequencer means is enabled by said third comparator whereby said sequencing of said comparator means is initiated at the beginning-of-test optical measurement level.

5. The apparatus of claim 3 wherein said measurement circuit means includes reset means responsive to said first and second comparators for resetting said sequencer means at said pretest optical measurement level.

6. The apparatus of claim 5 wherein said sequencer means includes,
    a clock for providing clock pulses,
    a first counter for counting said clock pulses when enabled by said third comparator, said counter providing a first counter output after counting a predetermined number of clock pulses,
    a second counter having reset means responsive to said first counter output,
    gating means for gating clock pulses to said second counter, said gating means responsive to the output from said comparator means to inhibit clock pulses to said second counter when said comparator means detects that the measurement signal exceeds the selected test reference level whereby said second counter stores a count representing the magnitude of the optical measurement level of the test sample.

7. The apparatus of claim 6 wherein said measurement circuit means includes means for connecting the count stored in said second counter to said sequencer means whereby said sequencer means is stepped to select test reference levels in response to the count in said second counter.

8. The apparatus of claim 7 wherein said measurement circuit means includes a shift register storage means, means for loading the contents of said second counter into said shift register means to form a digital representation of the optical measurement level.

9. The apparatus of claim 8 wherein said means for loading includes encoder means for encoding the contents of said second counter means into a digital signal for driving said indicator means.

10. The apparatus of claim 9 wherein said shift register means stores said digital signal as 1's and 0's and includes means for stepping the contents of said shift register means to said indicator means to cause said indicator means to provide said indication.

11. The apparatus of claim 10 wherein said indicator means includes an annunciator for producing audible sounds, and includes means for switching said annunciator on and off in response to the 1's and 0's, respectively, of said shift register means whereby said annunciator means provides a number of audible sounds which is proportional to the optical measurement level of the test sample.

12. A battery-operable apparatus for the portable use of visually impared people in detecting an optical measurement level of a test sample comprising in one hand-held enclosure:
    a test station for holding the test sample,
    light source means for illuminating the test sample to cause light to reflect from the test sample to form the optical measurement level as a function of the reflectance of the test sample and of the intensity of the illuminating light, an optical-to-analog converter for converting the reflected light from the test sample to an electrical analog measuring signal having an amplitude proportional to the intensity of said reflected light, measurement circuit means including a plurality of comparators for comparing said measurement signal with a plurality of established reference levels to provide a digital signal representing the magnitude of the optical measurement level, said plurality of comparators including first and second comparators simultaneously receiving said measurement signal for comparing said measurement signal with first and second reference levels, respectively, and including means for generating said first and second reference levels to establish a pretest optical measurement level for said test sample, said plurality of comparators including a third comparator receiving said measurement signal for comparing said measurement signal with a third reference level and including means for generating said third reference level to establish a beginning-of-test optical measurement level for said test sample, indicator means responsive to said digital signal for providing an audible indication, detectable by visually impared people, of said optical measurement level.

13. The apparatus of claim 12 wherein said plurality of comparators includes comparator means for comparing said measurement signal with one or more test reference levels, test reference level generation means for generating said one or more test reference levels.

14. Apparatus for detecting an optical measurement level of a test sample comprising:

light source means for illuminating the test sample to cause light to emanate from the test sample to form the optical measurement level as a function of an optical property of the test sample and of the illuminating light, an optical-to-analog converter for converting the light emanating from the test sample to an electrical analog measuring signal having an amplitude proportional to said optical measurement level, measurement circuit means including test reference generation means for generating a plurality of test reference levels, including comparator means for sequencially comparing said measurement signal with said plurality of test reference levels to provide a digital signal representing the magnitude of the optical measurement level, and including sequencer means for sequentially selecting said test reference levels one at a time whereby said comparator means sequentially compares the amplitude of said measurement signal with said plurality of test reference levels to detect the optical measurement level of the test sample, indicator means responsive to said digital signal for providing an indication of said optical measurement level.

15. The apparatus of claim 14 wherein said sequencer means includes, a clock for providing clock pulses, a first counter for counting said clock pulses to provide a first counter output after counting a predetermined number of counter pulses, a second counter having reset means responsive to said first counter output, gating means for gating clock pulses to said second counter, said gating means responsive to the output from said comparator means to inhibit clock pulses to said second counter when said comparator means detects that the measurement signal exceeds the selected test reference level whereby said second counter stores a count representing the magnitude of the optical measurement level of the test sample.

16. The apparatus of claim 15 wherein said measurement circuit means includes means for connecting the count stored in said second counter to said sequencer means whereby said sequencer means is stepped to select test reference levels in response to the count in said second counter.

17. The apparatus of claim 16 wherein said measurement circuit means includes a shift register storage means, means for loading the contents of said second counter into said shift register means to form a digital representation of the optical measurement level.

18. The apparatus of claim 17 wherein said means for loading includes encoder means for encoding the contents of said second counter means into a digital signal for driving said indicator means.

19. The apparatus of claim 18 wherein said shift register means stores said digital signal as 1's and 0's and includes means for stepping the contents of said shift register means to said indicator means to cause said indicator means to provide said indication.

20. The apparatus of claim 19 wherein said indicator means includes an annunicator for producing audible sounds, and includes means for switching said annunciator on and off in response to the 1's and 0's, respectively, of said shift register means whereby said annunciator means provides a number of audible sounds which is proportional to the optical measurement level of the test sample.

21. The apparatus of claim 17 wherein said measurement circuit means includes means, responsive to said comparator means, for loading a below-scale signal into said shift register storage means.

22. The apparatus of claim 14 wherein said measurement circuit means includes pretest comparator means for detecting a pretest condition and includes means responsive to said pretest comparator means for forming a pretest digital signal representing said pretest condition, and wherein said indicator means includes means responsive to said pretest digital signal to provide a pretest indication.

23. The apparatus of claim 14 wherein said sequencer means includes means for enabling generation of said digital signal after an established time period.

* * * * *